(12) United States Patent
Huguet Clotet et al.

(10) Patent No.: US 8,309,717 B2
(45) Date of Patent: Nov. 13, 2012

(54) PROCESS TO PREPARE PALIPERIDONE AND INTERMEDIATES THEREOF

(75) Inventors: Juan Huguet Clotet, Sant Joan Despi (ES); Noelia Calcerrada Muñoz, Badalona (ES)

(73) Assignee: INKE, S.A., Castellbisbal (ES)

( * ) Notice: Subject to any disclaimer, the term of this patent is extended or adjusted under 35 U.S.C. 154(b) by 55 days.

(21) Appl. No.: 12/994,693

(22) PCT Filed: May 28, 2009

(86) PCT No.: PCT/EP2009/056578
§ 371 (c)(1),
(2), (4) Date: Jan. 12, 2011

(87) PCT Pub. No.: WO2009/144288
PCT Pub. Date: Dec. 3, 2009

(65) Prior Publication Data
US 2011/0124863 A1 May 26, 2011

Related U.S. Application Data

(60) Provisional application No. 61/058,692, filed on Jun. 4, 2008.

(30) Foreign Application Priority Data

May 29, 2008 (EP) .................................... 08157224

(51) Int. Cl.
*C07D 239/70* (2006.01)

(52) U.S. Cl. ........................................................ 544/282
(58) Field of Classification Search ........................ None
See application file for complete search history.

(56) References Cited

U.S. PATENT DOCUMENTS

| 5,158,952 A | * | 10/1992 | Janssen et al. ........... 514/259.41 |
| 5,254,556 A | | 10/1993 | Janssen et al. |
| 5,688,799 A | * | 11/1997 | Vandenberk et al. .... 514/259.41 |
| 2006/0004199 A1 | | 1/2006 | Reddy et al. |
| 2009/0048272 A1 | | 2/2009 | Padi et al. |

FOREIGN PATENT DOCUMENTS

| EP | 0368388 | | 5/1990 |
| WO | WO2006/027370 | * | 3/2006 |
| WO | WO 2009/010988 | | 1/2009 |
| WO | WO 2009/015828 | | 2/2009 |
| WO | WO 2009/044413 | | 4/2009 |
| WO | WO 2009/047499 | | 4/2009 |
| WO | WO 2009/060297 | | 5/2009 |

OTHER PUBLICATIONS

PCT International Search Report for PCT/EP2009/056578 completed by the EP Searching Authority on Aug. 12, 2009.

* cited by examiner

*Primary Examiner* — Jeffrey Murray
(74) *Attorney, Agent, or Firm* — Barnes & Thornburg LLP

(57) ABSTRACT

The present invention relates to an improved process for obtaining Paliperidone, I, comprising alkylating compound VI, or a salt thereof, with compound V, or a salt thereof, using a base selected from triethylamine or diisopropylethylamine and, optionally, a solvent. Moreover, the invention relies on the preparation of intermediates used in such process.

20 Claims, 4 Drawing Sheets

PROCESS TO PREPARE PALIPERIDONE AND INTERMEDIATES THEREOF

CROSS-REFERENCE TO RELATED APPLICATIONS

This application is the U.S. national phase of PCT/EP2009/056578 filed May 28, 2009, which claims priority to European Patent Application No. 08157224.0 filed May 29, 2008 and to U.S. Provisional Patent Application No. 61/058,692 filed Jun. 4, 2008, which are expressly incorporated by reference herein.

FIELD OF THE INVENTION

The invention relates to the synthesis of Paliperidone, a drug useful to treat schizophrenia, and processes to prepare intermediates thereof with improved yield and atomic economy.

BACKGROUND

Paliperidone, I, is an orally active drug useful for the treating of schizophrenia. Its chemical name is (±)-3-[2-[4-(6-fluoro-1,2-benzisoxazol-3-yl)-1-piperidinyl]ethyl]-6,7,8,9-tetrahydro-9-hydroxy-2-methyl-4H-pyrido[1,2-a]pyrimidin-4-one and its chemical structure is depicted below:

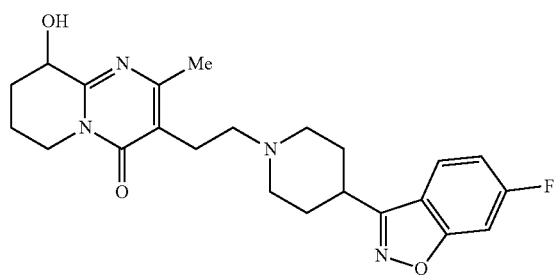

I

Paliperidone was first disclosed in European patent application EP0368388. In said application Paliperidone is prepared as depicted in Scheme 1.

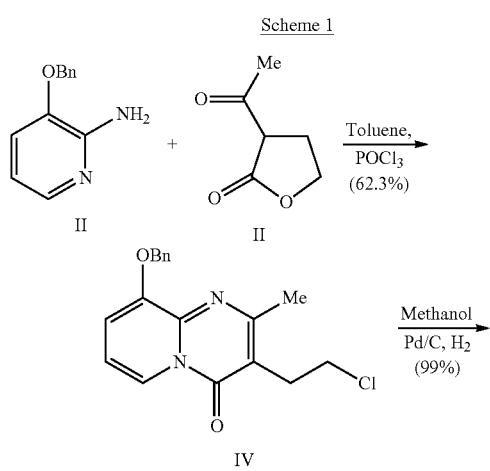

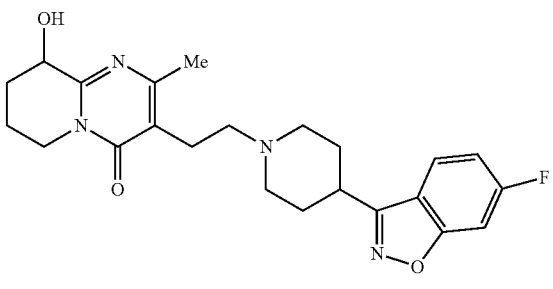

In the synthesis exemplified in said document it is used a benzyl protecting group in the hydroxyl of pyridine II. Protected pyridine II is reacted with the lactone III where the protecting group in the hydroxyl avoids selectivity problems during the coupling step. Then, the phosphoryl chloride substitutes the resulting hydroxyl group with chlorine and compound IV is obtained in a 62.3% yield, again the benzyl group avoids selectivity problems. Compound IV is then hydrogenated in the presence of a palladium catalyst to remove the benzyl protecting group and to reduce the pyridine ring. Compound V is obtained quantitatively.

Said compound V is coupled with compound VI in the presence of diisopropylamine in methanol to yield the desired compound I in a 21% yield.

International patent applications WO2008021345A and WO2008024415A also relate to the synthesis of Paliperidone and use a similar approach, also using, a benzyl protecting group with low to moderate yields.

The use of protecting groups is widely present in the field of organic synthesis, and they are useful to differentiate two or more moieties with similar reactivity. Even that, its use reduces the atomic economy of the reaction and increases the waste by-products. All this increases the costs and the environmental problems of the reaction.

Not only that, but in this case the use of the benzyl protecting group increases the amount of hydrogen gas, which is a toxic and flammable gas, consumed during the synthesis process.

There are documents describing the synthesis of suitable intermediates, such as EP0730594 and EP0808313 that prepare compound VIII in xylene and p-toluenesulphonic acid (Scheme 2). The resulting hydroxyethyl moiety is activated with a mesyl group.

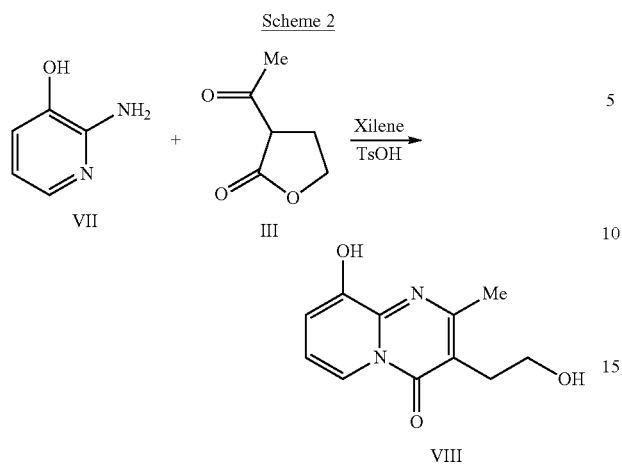

Scheme 2

In EP1791839 it is also described the synthesis of compound VIII in similar conditions and it is said that in the conditions described in EP0730594 and EP0808313 compound VIII is poorly soluble and that renders a difficulty in the following reactions (not described in the document). In EP1791839 this problem is solved using chlorobenzene.

In WO2008021345 it is described the preparation of Paliperidone, I, via the coupling of compounds V and VI using an inorganic base (Scheme 3).

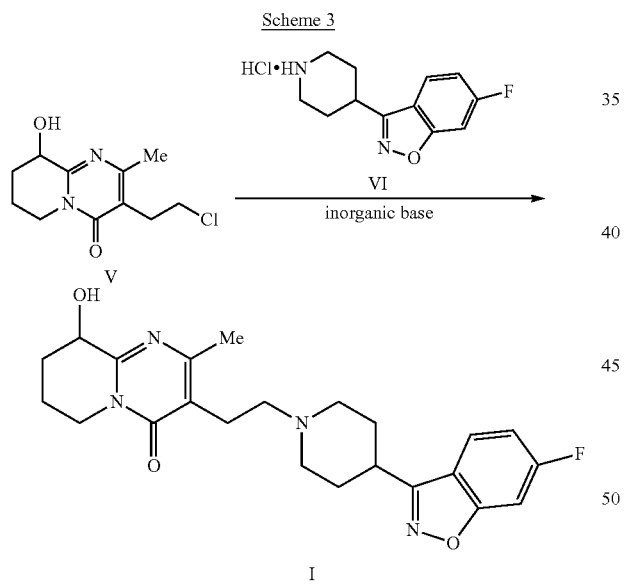

Scheme 3

Therefore, there is a need in the art to develop a new process to obtain Paliperidone with higher yield, increase atomic economy and less environmental drawbacks.

All the documents cited therein are enclosed in its entirety by reference.

BRIEF DESCRIPTION OF THE INVENTION

The invention relates to a process for obtaining Paliperidone, I, comprising alkylating compound VI, or a salt thereof, with compound V, or a salt thereof, using triethylamine or diisopropylethylamine and, optionally, a solvent (Scheme 4), Scheme 4 wherein compound V or a salt thereof is prepared by hydrogenation of compound IX or a salt thereof (Scheme 5).

Scheme 5

The invention also relates to a process for obtaining 3-(2-chloroethyl)-2-methyl-9-hydroxy-4H-pyrido[1,2-a]pyrimidin-4-one, IX, or a salt thereof, comprising two steps (Scheme 6):

a) reaction of 2-amino-3-hydroxypyridine, VII, and 2-acetylbutyrolactone, III, in a solvent and a cosolvent to obtain the diol VIII, b) diol VIII is reacted with a suitable chlorinating agent, [Cl⁻], to selectively obtain compound IX, and c) optionally, compound IX is converted into a salt thereof.

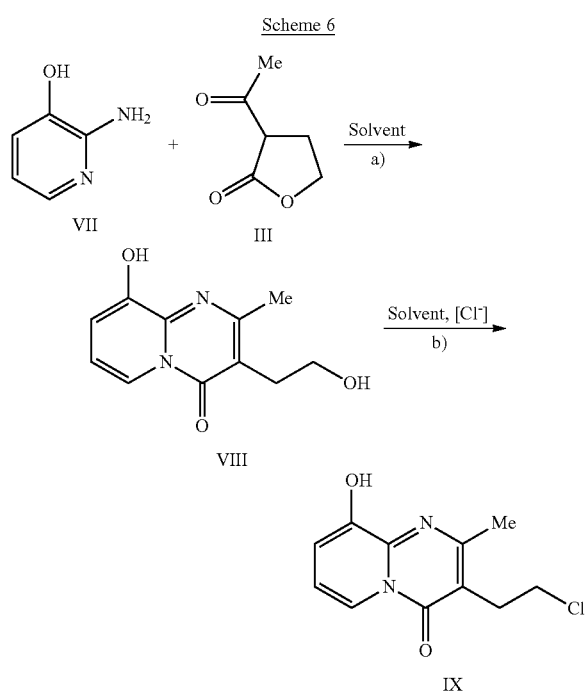

Scheme 6

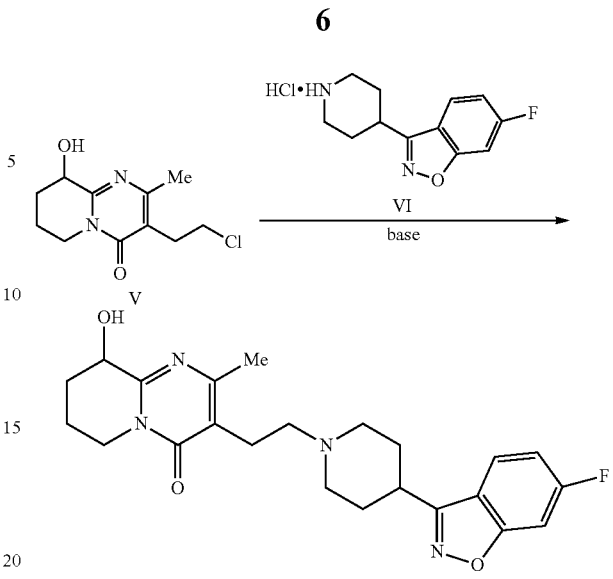

FIGURES

DETAILED DESCRIPTION OF THE INVENTION

Figure 1:
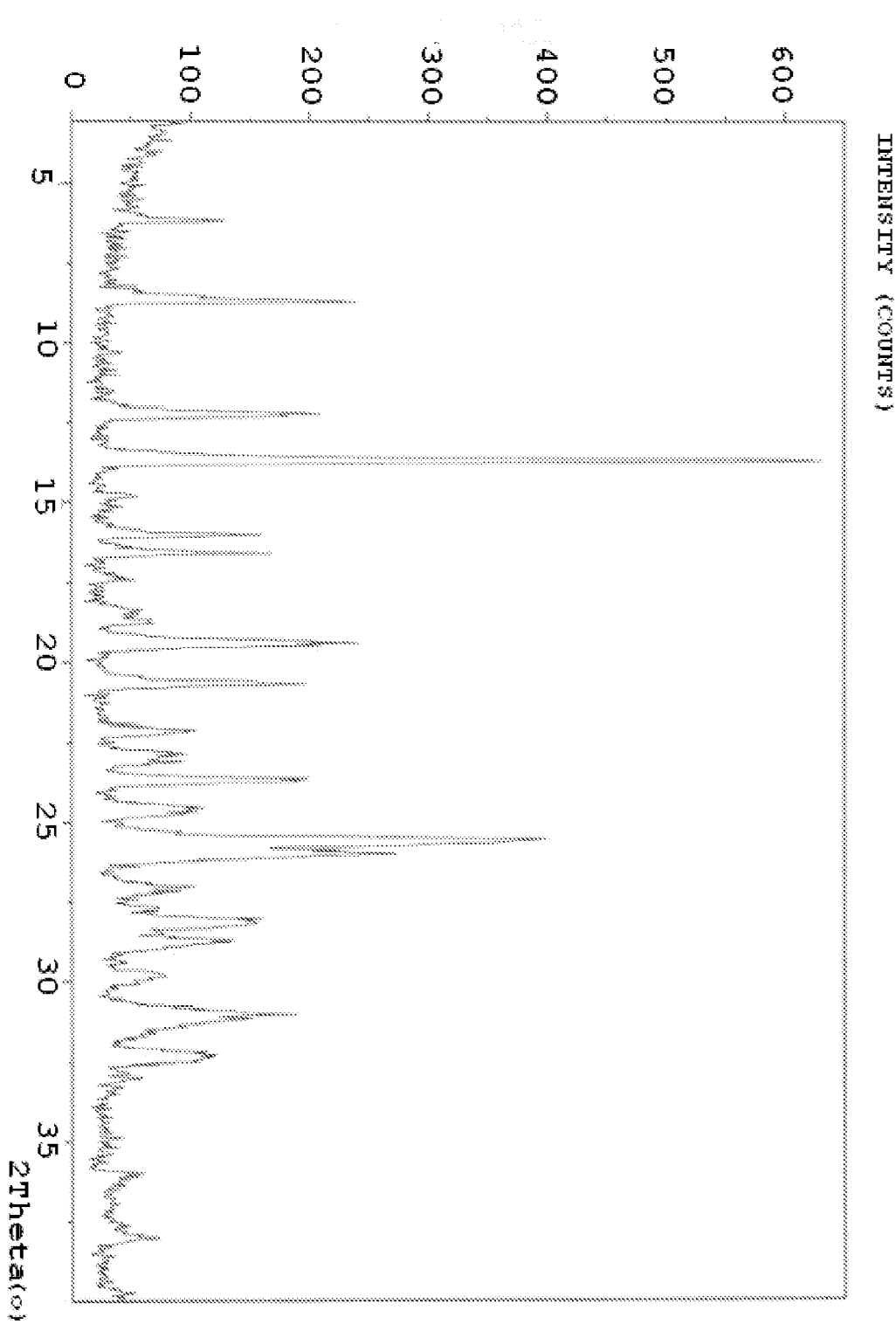
FIG. 1 illustrates the X-ray powder diffraction pattern of IX.HCl.
Figure 2:
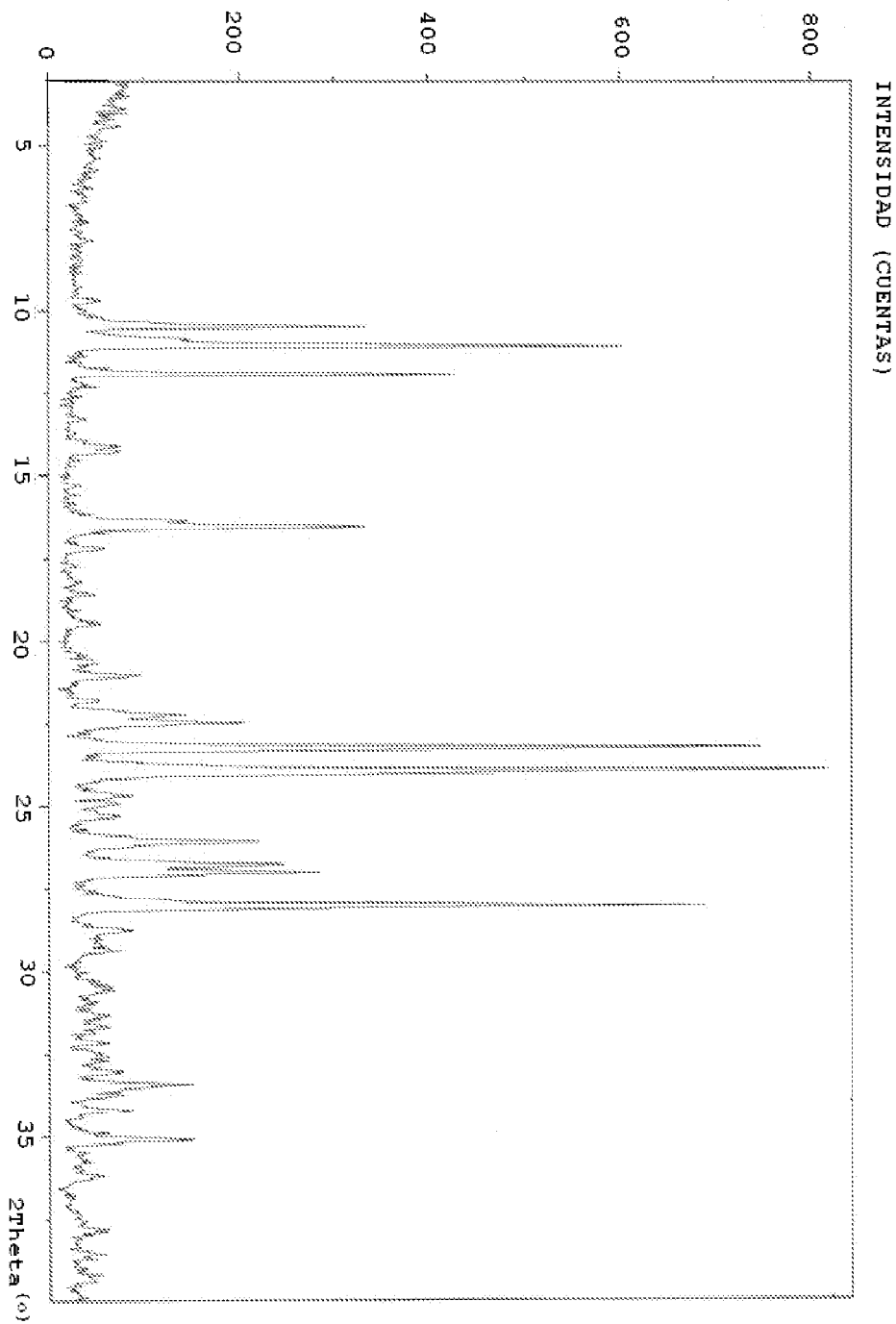
FIG. 2 illustrates the X-ray powder diffraction pattern of an embodiment of purified IX.HCl.
Figure 3:
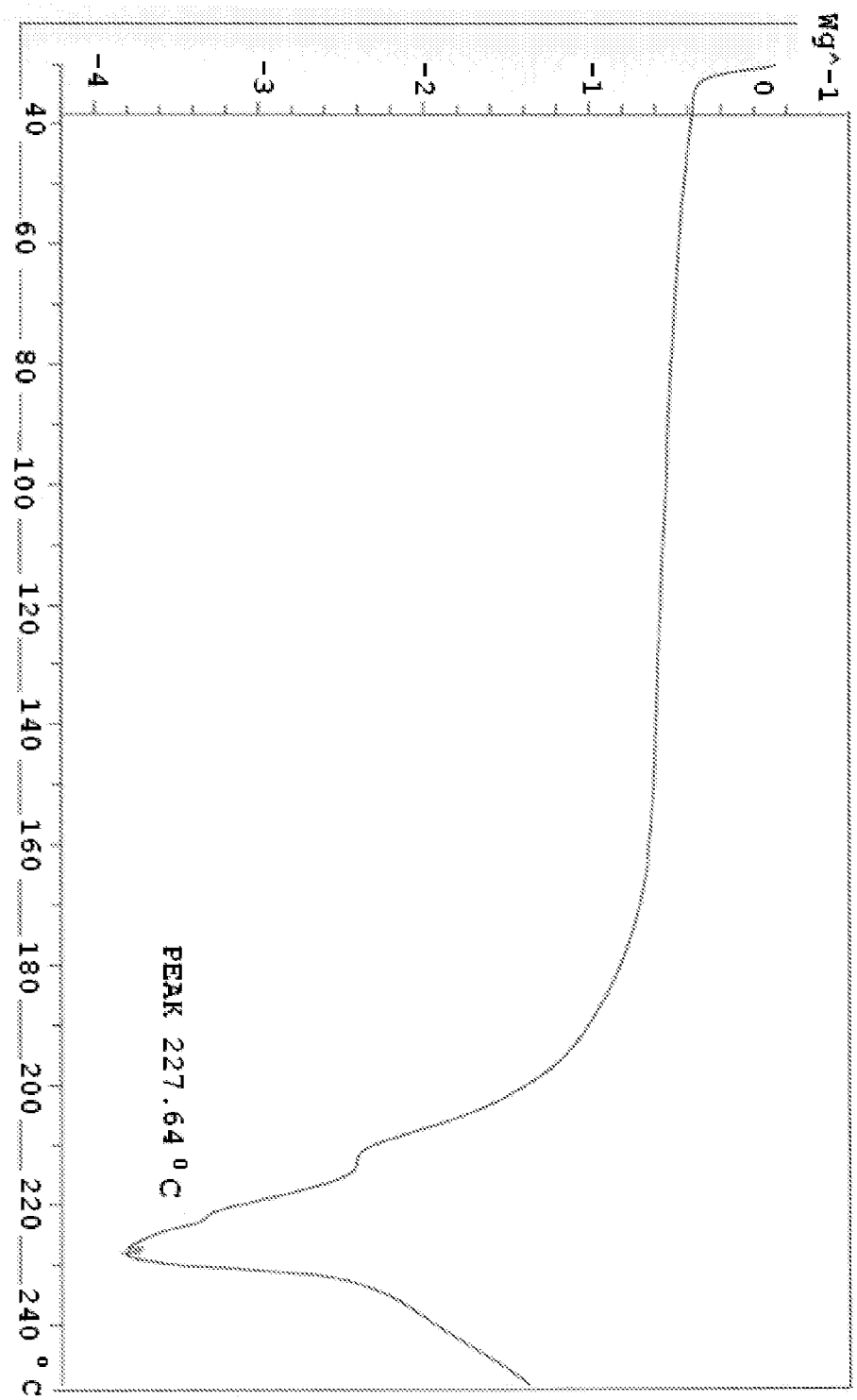
FIG. 3 illustrates the Differential scanning calorimetry of a second embodiment of purified IX.HCl.
Figure 4:
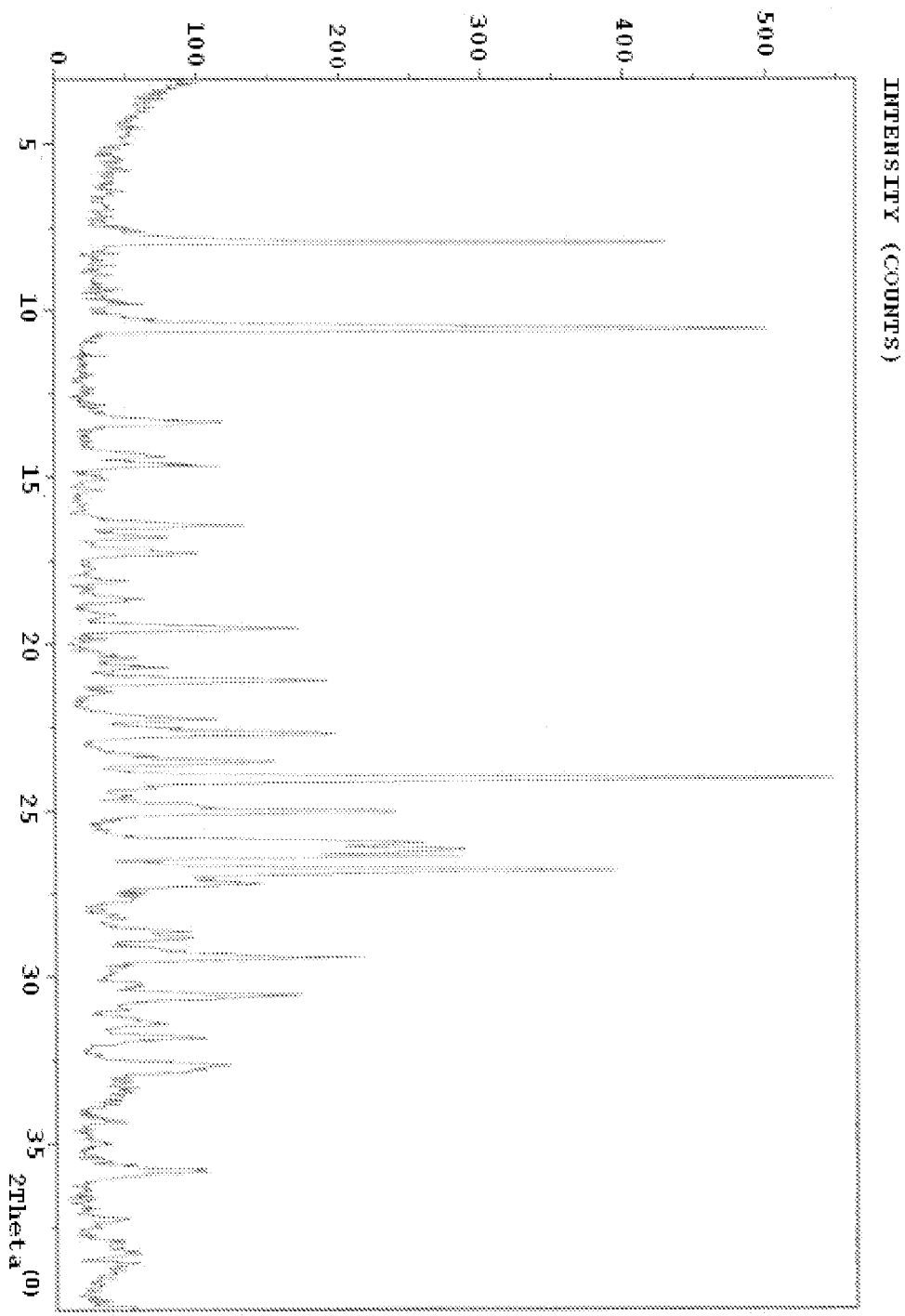
FIG. 4 illustrates the X-ray powder diffraction pattern of a second embodiment of purified IX.HCl.

In the context of the present invention, the following terms have the meaning detailed below:

The term "one-pot reaction" means two or more reactions that take place without isolating intermediate compounds, wherein all the reactants are added at the beginning of the first reaction or adding the reactants sequentially during the course of the reaction.

The term "polar aprotic solvent" relates to a polar solvent that is not capable of exchanging protons with the reagents and that has no polarizable proton. Examples of polar aprotic solvents are dimethylformamide (DMF), dimethylsulphoxide (DMSO), N-methylpyrrolidone and dimethylacetamide (DMAc).

The FT-IR spectra were recorded on a Perkin Elmer Spectrum One FT-IR spectrophotometer in an ATR accessory, from 650 to 4000 cm$^{-1}$.

The present invention relates to a process for obtaining Paliperidone, I, comprising alkylating compound VI, or a salt thereof, with compound V, or a salt thereof, using a base selected from triethylamine or diisopropylethylamine and, optionally, a solvent.

It has been surprisingly found that the change from the diisopropylamine base used in the prior art (EP0368388) to triethylamine or diisopropylethylamine allows to obtain the desired product Paliperidone, I, not only with a great increase on the yield (93%) but also without requiring column chromatography. In fact, only one crystallization is needed. Therefore, the use of triethylamine or diisopropylethylamine allows increasing the yield of the process and avoids the use of column chromatographic solvents and other related materials. Moreover, another advantage of avoiding purification through column chromatography is the use of no special equipment which means that the process can be undertaken with common reactors.

The increase on the yield and the use of common reactors to perform the reaction reduces the costs of the overall process, and the reduction of the solvents and other materials reduces the environmental drawbacks of the reaction.

The solvent used in the process for obtaining Paliperidone of the present invention is selected from an alcohol such as methanol, ethanol or isopropanol or water or a mixture of said solvents. When the process is performed in the absence of a solvent, the base, triethylamine or diisopropylethylamine, is used as solvent.

The process of the present invention preferably takes place from room temperature to the reflux temperature of the solvent. The preferred temperature is from 50° C. to the reflux temperature of the solvent.

Compound V, or a salt thereof, used in the process of the present invention can be prepared by hydrogenation of compound IX, or a salt thereof

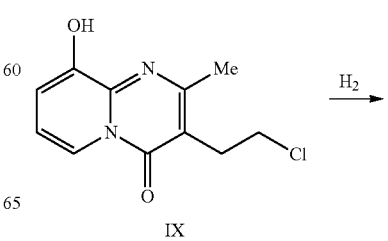

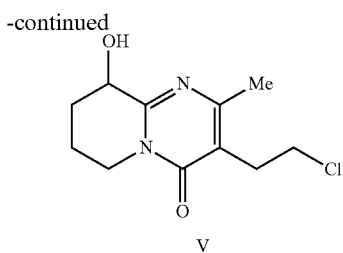

The hydrogenation of compound IX can be performed using a palladium hydrogenation catalyst in an alcoholic solution. The alcohol is preferably methanol, ethanol or isopropanol. According to one embodiment of the present invention, the alcoholic solution consists of an alcohol of commercial purity (see Example 3). According to another embodiment of the present invention, the alcoholic solution consists of a mixture of the alcohol with water, from 1:0.01 to a ratio of 1:1 (v/v) (i.e. from 99% alcohol up to 50% by volume of alcohol in the mixture), preferably from 99% to 80% of alcohol to water (see Example 4).

The preparation of intermediate 3-(2-chloroethyl)-2-methyl-9-hydroxy-4H-pyrido[1,2-a]pyrimidin-4-one, IX, or a salt thereof, can comprise the following steps:
a) reaction of 2-amino-3-hydroxypyridine, VII, and 2-acetylbutyrolactone, III, in a solvent and a cosolvent to obtain the diol VIII,
b) diol VIII is reacted with a suitable chlorinating agent, [Cl⁻], to selectively obtain compound IX, and
c) optionally, compound IX is converted into a salt thereof

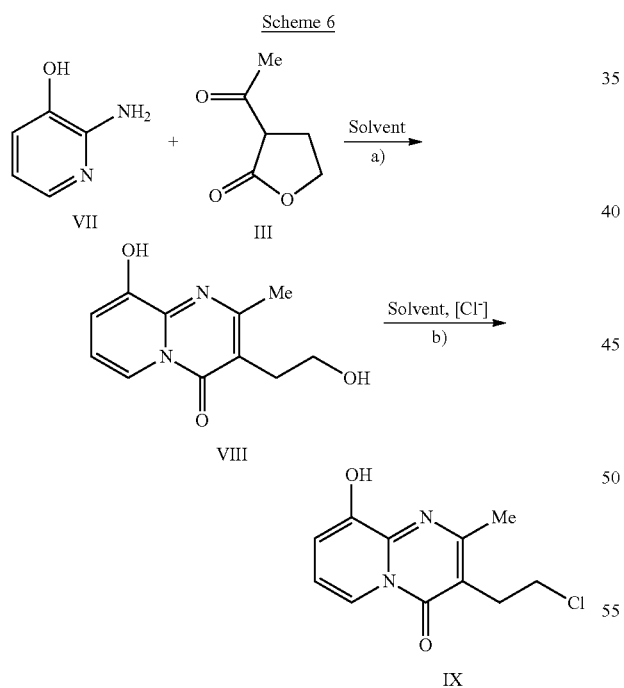

Scheme 6

The solvent used in the aforementioned step a) is an aromatic hydrocarbon or a mixture thereof such as benzene, toluene or xylenes. The cosolvent used in step a) is a polar aprotic solvent such as N-methylpyrrolidone, DMSO, DMAc or DMF.

The use of a cosolvent facilitates the solubility of the starting and final products resulting in an easier and faster reaction.

To facilitate this step a) of the process, an acidic catalyst such as methanesulphonic acid, p-toluensulphonic acid, sulphuric acid or acetic acid is added. Preferably, the catalyst is methanesulphonic acid.

Step a) of the process of the present invention to prepare compound IX, can be performed from 80° C. to the reflux temperature of the solvent or mixture of solvents, preferably it is performed at reflux temperature.

The suitable chlorinating agent, [Cl⁻], of the aforementioned step b) is selected from $POCl_3$, $PCl_3$, $PCl_5$, N-chlorosuccinimide, cyanuric chloride or the like.

Step b) of the process of the present invention to prepare compound IX, can be performed from room temperature to the reflux temperature of the solvent or mixture of solvents. Preferably the temperature is 80-120° C., more preferably 90-100° C.

The process of the present invention to prepare compound IX is performed with means to remove the evolved water, such as a Dean-Stark receiver or molecular sieves.

The process of the present invention to prepare compound IX can be performed as a one pot reaction, or the intermediate alcohol VIII can be isolated. Preferably, compound IX is prepared as a one pot reaction without isolation of VIII.

Since a chlorinating agent is used in step b), compound IX is likely to be obtained in the form of the hydrochloride salt. Other salts such as sulphate, hydrogensulphate, oxalate or acetate can also be formed from the free base and used for the purposes of the present invention.

The following non-limiting examples will further illustrate specific embodiments of the invention. They are, however, not intended to be limiting the scope of the present invention in any way.

EXAMPLES

Example 1

3-(2-chloroethyl)-2-methyl-9-hydroxy-4H-pyrido[1,2-a]pyrimidin-4-one hydrochloride, IX.HCl

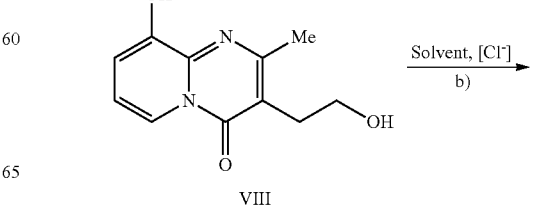

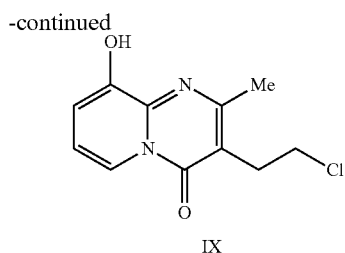

IX 5.0 g (45.41 mmol) of 2-amino-3-hydroxypyridine, VII, are suspended in xylene (35 ml) and N-methylpyrrolidone (5 ml). Next, methanesulphonic acid (0.021 ml; 0.31 mmol) and 2-acetylbutyrolactone, III, (2.9 ml, 26.93 mmol) were added. The resulting suspension is refluxed collecting the water evolved in a Dean-Stark receiver during two hours. Then a second portion of the 2-acetylbutyrolactone, III, (2.4 ml, 22.29 mmol) is added to the reaction mixture and the reflux is maintained until disappearance of the reactants.

The mixture is allowed to cooled down to 70-75° C. and POCl$_3$ (12.5 ml, 136.55 mmol) is added, then the mixture is heated to 90-95° C. and maintained until disappearance of the reactants. Then the mixture is allowed to cool to room temperature and water is added and the mixture cooled to 10° C. and a off-white solid precipitates that is filtered and washed with water. 9.4 g (34.4 mmol, 75% yield) of IX.HCl were obtained.

Analytical Data:

RMN $^1$H (D$_2$O) δ (ppm): 2.70 (s, CH$_3$); 3.21 (t, CH$_2$); 3.87 (t, CH$_2$Cl); 7.58 (t, arCH); 7.75 (d, arCH); 8.71 (d, arCH).

m.p.: 213-218° C.

DSC: m.p.=212.9° C.

K.F.=5.6% of H$_2$O

IR: 2844.8, 1703.5, 1641.4, 1584.10, 1515.9, 1406.8, 1297.7, 1227.0, 1162.2, 1142.3, 999.8, 877.2, 815.6, 778; 756.6; 722; 686 cm$^{-1}$

XRD Peak list: 8.68, 12.25, 13.71, 16.01, 16.58, 19.39, 20.67, 23.67, 25.58, 25.99, 28.02, 28.21, 31.02, Purification of IX.HCl The product IX.HCl (3-(2-chloroethyl)-2-methyl-9-hydroxy-4H-pyrido[1,2-a]pyrimidin-4-one monohydrochloride) thus obtained (9.4 g; 34.15 mmol), is placed in a round bottom flask and isopropyl alcohol 47 ml is added. The suspension is taken to 60° C. and water is added until a clear solution is obtained. The solution is then allowed to cool and taken to 0° C. The off-white precipitate was filtered and washed with isopropyl alcohol and dried. 7.01 g (75% yield of a 99% HPLC purity pure product) of compound IX are obtained.

Analytical Data of IX.HCl:

RMN $^1$H (D$_2$O) δ (ppm): 2.70 (s, CH$_3$); 3.21 (t, CH$_2$); 3.87 (t, CH$_2$Cl); 7.57 (t, arCH); 7.74 (d, arCH); 8.70 (d, arCH).

DSC: m.p.=228° C.

K.F: 4.7% of H$_2$O

IR: 3493; 3290; 1692.3; 1644.5; 1619.1; 1589.4; 1511.6, 1411.7; 1304.02; 1230.6; 1174.4; 1146.7; 1075.1; 914.1, 874.7, 811.1, 781.7, 760.9, 739.7; 721; 686.

XRD Peak list: 10.49, 11.08, 11.91, 16.54, 22.47, 23.23, 23.94, 26.08, 26.77, 27.00, 28.01, 35.07.

The product obtained as described above can be further dried in the vacuum oven at 60° C. for 24 hours.

Analytical Data:

K.F: 0.1% of H$_2$O

DSC: m.p.=227° C.

IR: 2650, 2603, 2523, 1701, 1636, 1616, 1580, 1508, 1441, 1403, 1358, 1334, 1302, 1229, 1189, 1172, 1160, 1138, 1101, 1074, 1039, 1014, 998, 938, 918, 888, 874, 825, 800, 789, 755, 708, 678;

XRD Peak list: 7.85, 10.51, 13.25, 14.60, 16.65, 17.20, 19.50, 21.04, 22.63, 23.13, 23.29, 24.00, 24.97, 25.91, 26.30, 26.68, 27.09, 29.21, 29.72, 30.51, 32.74, 33.39.

Alternative Purification Method of IX.HCl (2-chloroethyl)-2-methyl-9-hydroxy-4H-pyrido[1,2-a]pyrimidin-4-one monohydrochloride, IX.HCl, (15.0 g; 54.5 mmol) was placed in a round bottom flask and isopropyl alcohol was added. The suspension was taken to reflux and it was kept for 30 minutes. The reaction mixture was then allowed to cool and taken to 0° C. The off-white precipitate was filtered and washed with isopropyl alcohol and dried. 13.3 g (88.7% yield of a 98% HPLC purity pure product) of compound IX.HCl were obtained.

Analytical Data:

K.F=0.1% of H$_2$O

DSC: m.p.=227.6° C.

RMN $^1$H (D$_2$O) δ (ppm): 2.70 (s, CH$_3$); 3.22 (t, CH$_2$); 3.88 (t, CH$_2$Cl); 7.59 (t, arCH); 7.75 (d, arCH); 8.71 (d, arCH).

IR: 1709.7; 1642.6; 1620.4; 1583.2; 1514.2; 1410.73; 1303.02; 1228.6; 1171.1; 1144.7; 1076.7; 919.1; 876.6; 815.2; 781.65; 736.7; 719.9; 679.9 cm$^{-1}$.

XRD Peak list: 7.94, 10.57, 13.37, 14.64, 16.45, 17.28, 19.55, 21.11, 22.26, 22.70, 23.54, 24.08, 25.03, 26.00, 26.20, 26.39, 26.83, 27.21, 28.85, 29.43, 30.59, 32.67. The obtained XRD pattern was the same as that obtained in the previous embodiment.

The product obtained as described above can be further dried in the vacuum oven at 60° C. for 24 hours. The product was characterised by IR and DSC:

DSC: m.p.=222.7-230.74° C.

IR: 2439.4; 1712.5; 1640.6; 1618.3; 1578.9; 1522.4; 1442.6; 1410.4; 1356; 1333.3; 1300.9; 1270.1; 1228.33; 1189.4; 1169; 1140.8; 1076.1; 1039.5; 1020.9; 921.47; 876.6; 849.9; 789.9; 755.9; 736.0; 705.73; 676.8 cm$^{-1}$.

Example 2

3-(2-chloroethyl)-2-methyl-9-hydroxy-4H-pyrido[1,2-a]pyrimidin-4-one monohydrochloride, IX 5.0 g (45.41 mmol) of 2-amino-3-hydroxypyridine, VII, are suspended in xylene (35 ml) and N-methylpyrrolidone (5 ml). Next, methanesulphonic acid (0.021 ml; 0.31 mmol) and 2-acetylbutyrolactone, III, (2.9 ml, 26.93 mmol) are added to the suspension. The resulting suspension is refluxed collecting the water evolved in a Dean-Stark receiver during two hours. Then a second portion of the 2-acetylbutyrolactone, III, (2.4 ml, 22.29 mmol) is added to the reaction mixture and the reflux is maintained until disappearance of the reactants.

The mixture is allowed to cooled down to 70-75° C. and POCl$_3$ (12.5 ml, 136.55 mmol) is added, then the mixture is heated to 90-95° C. and maintained until disappearance of the reactants. Then, the reaction mixture is allowed to cool to room temperature and water is added. The mixture is neutralised with NH$_3$aq and the product is extracted with DCM (3×100 ml). The solvent is evaporated under reduced pressure and an oily residue is obtained. Next, IPA is added and HClaq is added until pH 2-3. An off-white solid precipitates during the addition. The suspension is allowed to cool and the solid is filtered and washed with IPA. 9.4 g (34.4 mmol, 75% yield of a 98% HPLC pure product) of IX are obtained.

Example 3

3-(2-chloroethyl)-6,7,8,9-tetrahydro-2-methyl-9-hydroxy-4H-pyrido[1,2-a]pyrimidin-4-one, V

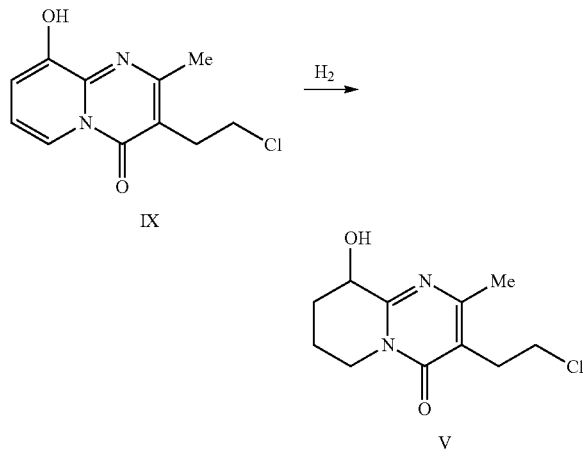

25.0 g (90.86 mmol) of compound IX hydrochloride are dissolved in methanol (225 ml) and the solution is then treated with carbon and Celite during 1 h at 40° C. The mixture was then filtered and the cake was washed with hot methanol. The solution is placed in a hydrogenation reactor and 3.75 mg of Pd/C are added to the mixture. The reactor is then purged with nitrogen once and three times with $H_2$. The reaction mixture was heated to 50° C. and the reaction was controlled until disappearance of the reactants at atmospheric pressure.

When the reaction is over the catalyst is filtered and the solvent is evaporated until an oily residue is obtained. Then, water is added and a solution of potassium acetate in water is added dropwise to the above solution. The compound precipitates and is filtered and washed with water. 19.7 g. (81.17 mmol; 89.5% yield) of the desired product V are obtained.

Analytical Data of V:

NMR $^1$H (CDCl$_3$) δ (ppm): 1.72-2.33 (m, CH$_2$—CH$_2$); 2.37 (s, CH$_3$); 3.01 (t, CH$_2$); 3.77 (t, CH$_2$Cl); 3.94 (dt, CH$_2$); 4.52 (t, CH—OH).

m.p.: 102-106° C.

IR: 1651.6, 1597.0, 153.9, 1486.4, 1447.2, 1326.0, 1270.4, 1182.1, 1118.8, 1074.2, 1020.7, 981.0, 951.1, 907.6, 802.1, 736.0, 706.5, 659.7.

Preparation of V.HCl 0.500 g (2.06 mmol) of compound V, obtained according to the process described above, are dissolved in 2-butanone (3.5 ml) and concentrated hydrochloric acid is added to the solution until pH 2 is obtained. The solvent was then removed under vacuum till an oily residue is obtained. 2-Butanone is added to the residue and evaporated under vacuum. This procedure is repeated three times.

2-Butanone is added to the oily residue and the product is allowed to precipitate. Then, the suspension is cooled to 0° C. The precipitated product is filtered and washed with 2-butanone. 0.263 g. (0.942 mmol; 46% yield) of the desired product V.HCl are obtained.

Analytical Data of V.HCl:

NMR $^1$H (D$_2$O) δ (ppm): 1.91-2.37 (m, CH$_2$—CH$_2$); 2.53 (s, CH$_3$); 3.07 (t, CH$_2$); 3.80 (t, CH$_2$Cl); 4.01 (dt, CH$_2$); 4.97 (t, CH—OH).

m.p.: 118-121° C.

IR: 1691.5, 1661.8, 1591.8, 1548.8, 1454.4, 1432.4, 1388.5, 1329.8, 1188.3, 1113.0, 1058.0, 1025.6, 906.1, 832.3, 789.5, 728.8.

Example 4

3-(2-chloroethyl)6,7,8,9-tetrhydro-2-methyl-9-hydroxy-4H-pyrido[1,2-a]pyrimidin-4-one, V 2.75 g (10 mmol) of IX.HCl, 40 ml of IPA/H$_2$O (19:1 v/v, 0.25 M) and 404 mg of Pd/C catalyst (5% w/w (dry), containing 66.20% water) are placed in a reaction vessel and purged with nitrogen (~40 psi) five times at room temperature. Afterwards, the reaction vessel is purged an extra five times with hydrogen (50-60 psi) and heated up to 55° C. under hydrogen (at atmospheric pressure) over 20 minutes. After that, the vessel is pressurized with hydrogen (15 psi) and mechanical stirring supplied (1500 rpm) at 55° C. for 3 hours. The reaction vessel is then cooled to room temperature and carefully vented.

Analysis of the supernatant by HPLC showed that high conversions are achieved, over 98%, and less than 1% of the de-chlorinated by-product is produced.

The reaction solution is filtered over celite, the filtered cake washed with MeOH and the combined filtrates evaporated to dryness to give V.HCl, as an off-white solid. A solution of potassium acetate in water is added drop wise, until complete precipitation of compound V is achieved. The obtained precipitate is filtered and washed with water, yielding 2.23 g (92% yield) of compound V.

Analytical Data of V.HCl:

RMN $^1$H (D$_2$O) δ (ppm): 1.91-2.37 (m, CH$_2$—CH$_2$), 2.53 (s, CH$_3$); 3.07 (t, CH$_2$); 3.80 (t, CH$_2$Cl); 4.01 (dt, CH$_2$); 4.97 (t, CH—OH).

Analytical Data of V:

RMN $^1$H (CDCl$_3$) δ (ppm): 1.72-2.33 (m, CH$_2$—CH$_2$), 2.37 (s, CH$_3$); 3.01 (t, CH$_2$); 3.77 (t, CH$_2$Cl); 3.94 (dt, CH$_2$); 4.52 (t, CH—OH).

Example 5

Preparation of Paliperidone, I 5.7 g (23.49 mmol) of compound V are placed in a reaction vessel and methanol is added (29 ml). To this suspension 6.0 g (23.41 mmol) of compound VI are added and then Et$_3$N (9.8 ml; 70.41 mmol) is added. The resulting reaction mixture is then taken to reflux and maintained at this temperature overnight. The reaction mixture is then cooled down to 0° C. and the solid precipitated is filtered and washed with MeOH. 7.4 g (17.35 mmol, 74%) of Paliperidone I are obtained.

Example 6

Preparation of Paliperidone, I

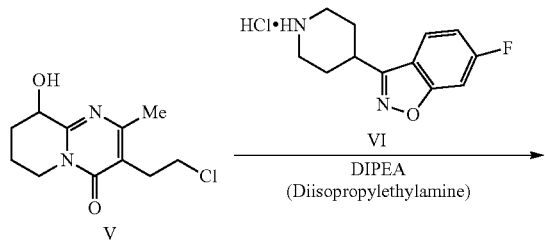

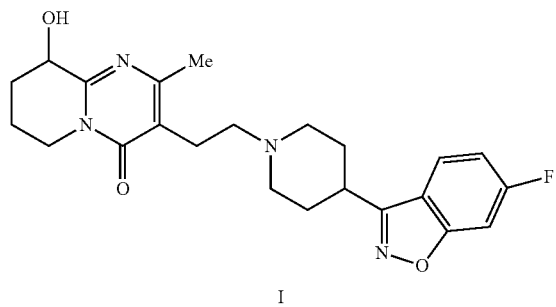

10.0 g (41.20 mmol) of compound V and 50 ml of methanol are placed in a reaction vessel. Afterwards, 10.6 g (41.33 mmol) of compound VI and 17.6 ml of DIPEA (102.81 mmol) are added. The resulting suspension is heated under reflux overnight. The reaction mixture is then cooled down to 0° C. and the solid precipitate filtered and washed firstly with MeOH and then with water. 16.3 g (38.22 mmol, 93% yield) of Paliperidone I are obtained.

The invention claimed is:

1. A process for obtaining Paliperidone, I, comprising alkylating compound VI, or a salt thereof, with V, or a salt thereof, using triethylamine or diisopropylethylamine and, optionally, a solvent,

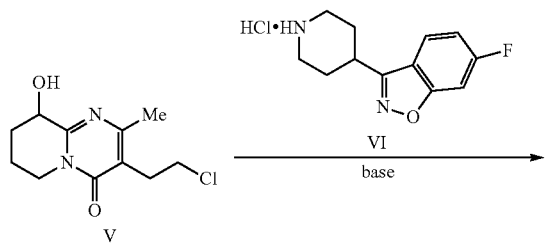

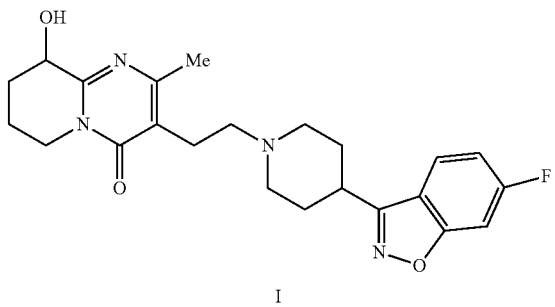

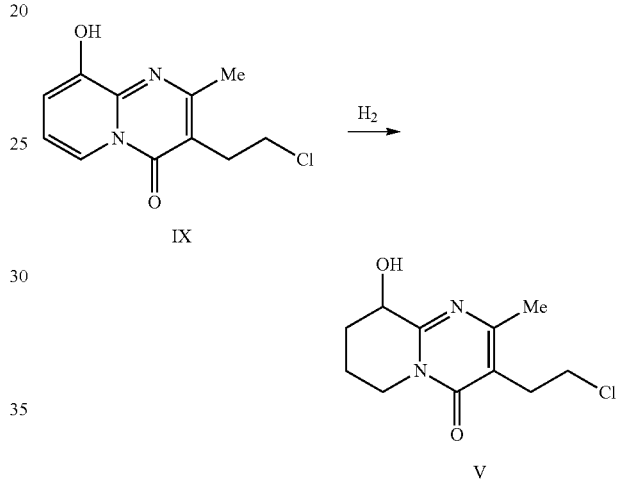

wherein compound V, or a salt thereof, is prepared by hydrogenation of compound IX, or a salt thereof in an alcoholic solution, wherein the alcoholic solution consists of a mixture of an alcohol with water from 1:0.01 to a ratio of 1:1 (v/v).

2. The process according to claim 1 wherein the solvent is an alcohol.

3. The process according to claim 1 which takes place from room temperature to the reflux temperature of the solvent.

4. The process according to claim 1 wherein the alkylating reaction takes place using diisopropylethylamine.

5. The process according to claim 1 wherein compound IX is hydrogenated using a palladium hydrogenation catalyst.

6. The process according to claim 1 wherein the alcohol in the alcoholic solution is methanol, ethanol or isopropanol.

7. The process according to claim 3 wherein the process takes place from 50° C. to the reflux temperature of the solvent.

8. The process according to claim 1 wherein the preparation of compound IX or a salt thereof comprises the following steps:
   a) reaction of 2-amino-3-hydroxypyridine, VII, and 2-acetylbutyrolactone, III, in a solvent and a cosolvent with an acidic catalyst to obtain the diol VIII, wherein the cosolvent is a polar aprotic solvent;
   b) diol VIII is reacted with a chlorinating agent, [Cl⁻], to selectively obtain compound IX, and

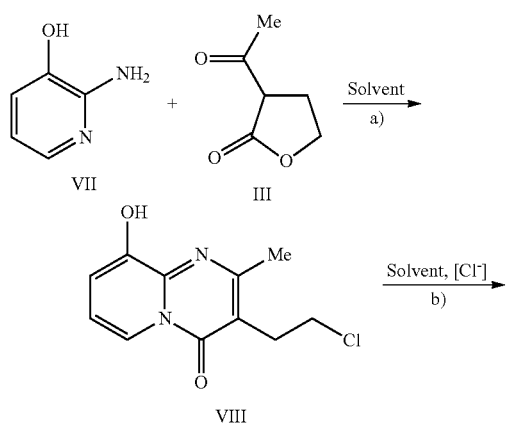

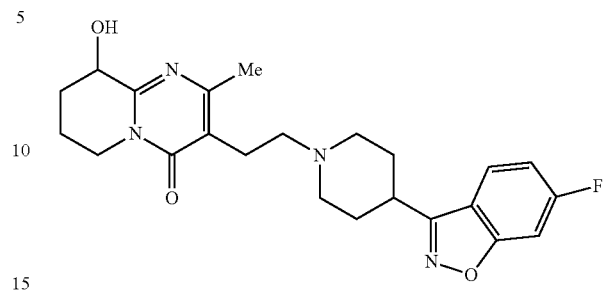

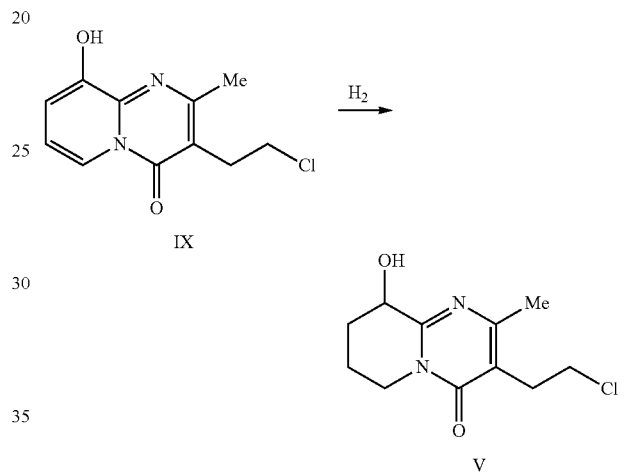

c) optionally, compound IX is converted into a salt thereof.

9. The process according to claim 8 wherein the solvent is an aromatic hydrocarbon or a mixture thereof.

10. The process according to claim 8 wherein the acidic catalyst is methanesulphonic acid.

11. The process according to claim 8 wherein step a) is performed at reflux temperature.

12. The process according to claim 8 wherein the chlorinating agent, [Cl⁻], in step b) is $POCl_3$.

13. The process according to claim 8 wherein step b) is performed at 80-120° C.

14. The process according to claim 8 performed with means to remove evolved water.

15. The process according to claim 8 which is performed as a one pot reaction.

16. The process according to claim 8 wherein compound IX is obtained in the form of a hydrochloride salt.

17. The process of claim 13 wherein step b) is performed at 90-100° C.

18. A process for obtaining Paliperidone, I, comprising the step of hydrogenating compound IX, or a salt thereof, in an alcoholic solution consisting of a mixture of alcohol to water from 1:0.01 to a ratio of 1:1 (v/v) to afford compound V, or a salt thereof.

19. The process according to claim 18 wherein compound IX is hydrogenated using a palladium hydrogenation catalyst.

20. The process according to claim 18 wherein the alcohol in the alcoholic solution is methanol, ethanol or isopropanol.

* * * * *

UNITED STATES PATENT AND TRADEMARK OFFICE
CERTIFICATE OF CORRECTION

| | |
|---|---|
| PATENT NO. | : 8,309,717 B2 |
| APPLICATION NO. | : 12/994693 |
| DATED | : November 13, 2012 |
| INVENTOR(S) | : Juan Huguet et al. |

It is certified that error appears in the above-identified patent and that said Letters Patent is hereby corrected as shown below:

In column 14, line 56, please replace the text "takes place from 50° C. to the reflux temperature of the" with the text --takes place from 50° C to the reflux temperature of the--

Signed and Sealed this
First Day of January, 2013

David J. Kappos
*Director of the United States Patent and Trademark Office*